United States Patent [19]

Obana et al.

[11] 4,384,936

[45] May 24, 1983

[54] SYSTEM FOR DETERMINING THE CONCENTRATION OF AN L-AMINO ACID IN FERMENTATION

[75] Inventors: Haruo Obana, Kawasaki; Tadashi Shirakawa, Zushi; Motohiko Hikuma; Takeo Yasuda, both of Yokohama; Isao Karube, Tachikawa; Shuichi Suzuki, Tokyo, all of Japan

[73] Assignee: Ajinomoto Company, Incorporated, Tokyo, Japan

[21] Appl. No.: 237,668

[22] Filed: Feb. 24, 1981

Related U.S. Application Data

[62] Division of Ser. No. 24,330, Mar. 27, 1979, Pat. No. 4,299,669.

[30] Foreign Application Priority Data

Mar. 28, 1978 [JP] Japan ............................. 53-35906
May 31, 1978 [JP] Japan ............................. 53-65380

[51] Int. Cl.³ ............................................. C12M 1/40
[52] U.S. Cl. ................................. 204/403; 204/1 E; 435/25; 435/26; 435/28; 435/37; 435/182; 435/288; 435/817
[58] Field of Search ............... 204/195 B, 1 E, 195 P, 204/1 K; 435/817, 25, 26, 28, 37, 182, 288

[56] References Cited

U.S. PATENT DOCUMENTS

| | | | |
|---|---|---|---|
| 3,510,407 | 5/1970 | Stack | 204/195 B X |
| 3,542,662 | 11/1970 | Hicks et al. | 204/195 P |
| 3,659,586 | 5/1972 | Johns et al. | 204/195 B X |
| 3,857,771 | 12/1974 | Sternberg | 204/195 B |
| 3,869,354 | 3/1975 | Montalvo | 204/195 B |
| 4,129,478 | 12/1978 | Racine et al. | 204/195 B X |

OTHER PUBLICATIONS

K. Venkatsubramanian, "Immobilized Microbial Cells", A.C.S. Symposium Series 106, (1979).
Isao Karube et al., J. Solid-Phase Biochem., vol. 2, No. 2, pp. 97–104, (1977).
Isao Karube et al., Biotech. & Bioengineering, vol. XIX, pp. 1535–1547, (1977).
Isao Karube et al., J. Ferment. Technol., vol. 55, No. 3, pp. 243–248, (1977).
J. C. Weaver et al., Enzyme Engineering, vol. 4, pp. 403–404, (1978).
J. C. Weaver et al., Biochimica et Biophysica Acta, 438, pp. 296–303, (1976).
G. A. Rechnitz et al., Science, vol. 199, (1978).
G. A. Rechnitz et al., Analytica Chimica Acta, 94, pp. 357–365, (1977).

*Primary Examiner*—G. L. Kaplan
*Attorney, Agent, or Firm*—Oblon, Fisher, Spivak, McClelland & Maier

[57] ABSTRACT

Electrochemical method for determining the concentration of a carbon source and L-amino acid in a fermentation medium or cultured broth by contacting a microbial electrode consisting of an oxygen-sensitive electrode or a carbon dioxide gas-sensitive electrode combined with fixed microbial cells of a microorganism capable of assimilating said carbon source or decarboxylating said L-amino acid with a sample solution and sensing electrically the rate of current decrease which is caused by the consumed oxygen in the solution in proportion to the concentration of carbon source; or the electric motive force which is caused by the liberation of carbon dioxide in the sample solution in proportion to the concentration of L-amino acid. Microbial electrodes and systems useful in carrying out the aforementioned method are disclosed.

7 Claims, 14 Drawing Figures

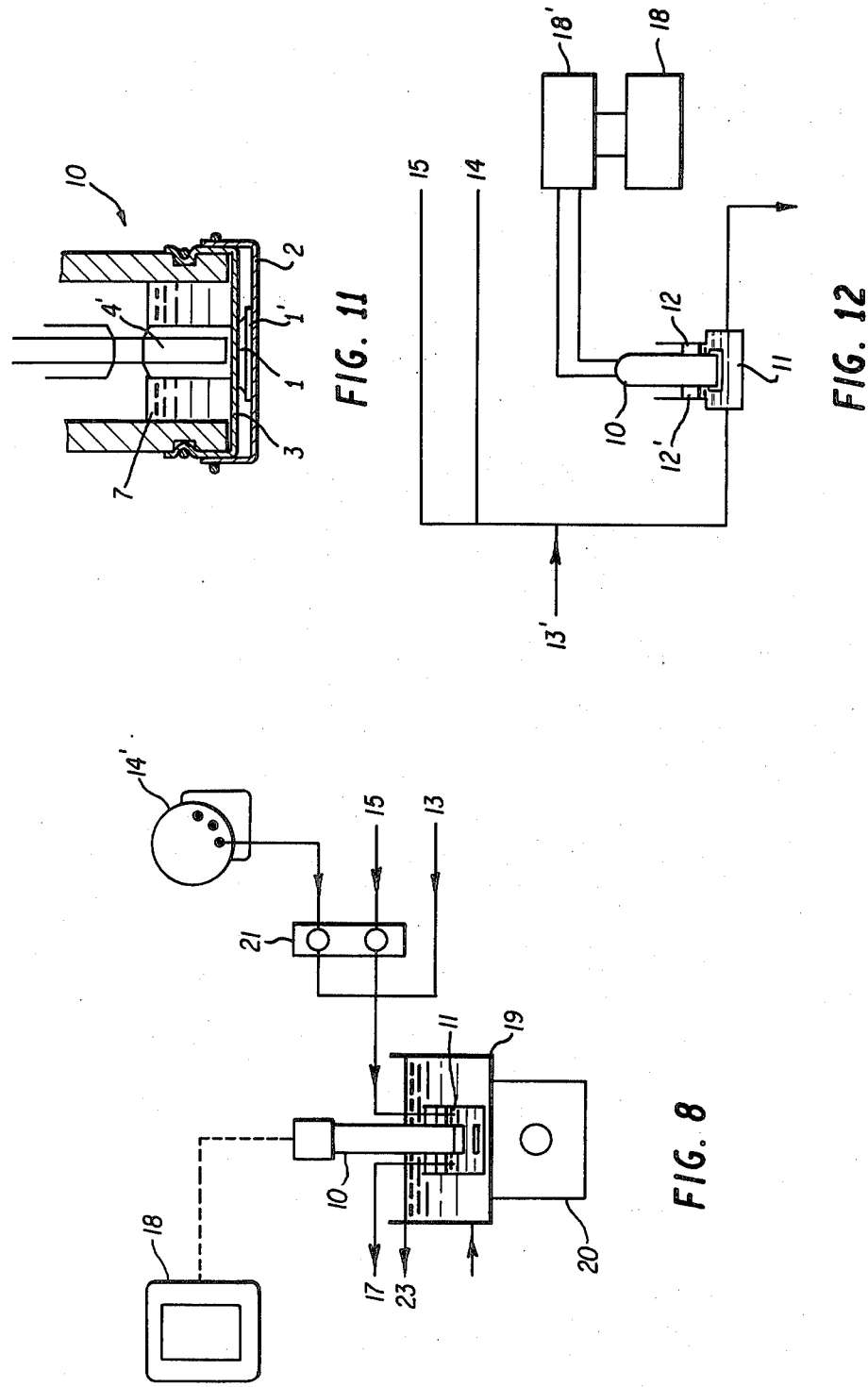

SYSTEM FOR DETERMINING THE CONCENTRATION OF AN L-AMINO ACID IN FERMENTATION

This is a division of application Ser. No. 024,330, filed Mar. 27, 1979 and now U.S. Pat. No. 4,299,669.

BACKGROUND OF THE INVENTION

1. Field of the Invention

This invention relates to a method for the rapid, simple and quantitative determination of a carbon source and a fermentation product in a culture medium by means of a microbial electrode.

2. Description of the Prior Art

In an industrial fermentation ramification such as L-amino acid fermentation and SCP fermentation, a feeding method by which a carbon source is continuously fed into the culture medium so that the concentration of the carbon source in the medium is controlled within a desired concentration during the fermentation is widely applied to obtain increased production.

In order to precisely control the concentration of a carbon source, on-line measurement of the carbon source in the culture medium is necessary, therefore a method for rapid, simple and quantitative determination of a carbon source is required.

Similarly, a method that is rapid, simple and quantitative in determining a fermentation product such as L-glutamic acid in the culture medium is also very effective for controlling the fermentation process, since the conclusion time of the fermentation can be easily decided.

According to a conventional method it is possible to determine non volatile carbon sources such as glucose and sucrose using an enzyme such as invertase and glucose oxidase together with a coloring material, or using an enzyme-electrode method comprising an electrode and immobilized enzyme. However, these conventional methods are not adapted for use in the determination of non-volatile carbon sources in a culture medium, when such a culture medium especially contains cane or beet molasses as a carbon source as well as containing a number of other organic compounds. Therefore, in practice, a conventional method for determining the reducing power of a saccharide is still employed. However, this common method is not satisfactory for the purpose of on-line measurements, since this common method is largely affected by reducing impurities usually coexisting in a culture medium during fermentation. Moreover, it requires complicated hydrolysis steps of the carbon source if the carbon source used is not a monosaccharide.

Accordingly, by use of a common gas chromatography or a semiconductor sensor, volatile carbon sources such as methanol, ethanol and acetic acid may be determined. These methods however are also unsatisfactory for on-line measurements, since a large amount of non-volatile organic impurities contained in a culture medium spoil the column of the gas-chromotography apparatus making long-term determination impossible. Further, this method is too unstable for the semiconductor sensor to be applied for on-line measurements.

On the other hand, it is possible to determine a fermentation product such as an L-amino acid according to the conventional Warburg method or the auto-analyzer method. These determine manometrically or colorimetrically the amount produced by the decarboxylation reaction (I) catalyzed by an L-amino acid decarboxylase such as L-glutamic acid or L-lysine decarboxylase derived from pumpkin, *Esherichia coli* or *Bacterium cadaveris*.

L-amino acid
decarboylase

These common methods are excellent in accuracy but not economical since an expensive enzyme has to be used batchwise and cannot be used continuously, and a very expensive determination apparatus is required for the auto-analyzer method. Furthermore, in all cases a complicated filtration process is necessary to remove microbial cells from the culture medium prior to the determination.

SUMMARY OF THE INVENTION

One object of the invention is to provide a method for the rapid, simple and quantitative determination of a carbon source in a culture medium.

Another object of the invention is to provide a method for the determination of a carbon source in a culture medium by means of a microbial electrode.

Still another object of the invention is to provide a method for the determination of a fermentation product in a culture medium by means of a microbial electrode.

A further object of the invention is to provide a method for the determination of a carbon source and fermentation product in a culture medium by means of an electrode wherein intact microbial cells are trapped therein.

Still a further object of the invention is to provide a microbial electrode useful for the determination of carbon sources and fermentation products in a culture medium.

Briefly, these objects and other objects of the invention as hereinafter will become more readily apparent can be attained by providing a method for determining the concentration of a carbon source in a culture medium or cultured broth solution which comprises contacting said culture aerobically with a microbial electrode comprising a fixed or immobilized micro-organism capable of aerobically metabolizing said carbon source and thereby consuming oxygen in said culture, and an oxygen-sensitive electrode, electrochemically measuring the consumption of the oxygen in said culture and
  thereby correspondingly determining the concentration of said carbon source in said culture.

Another object of this invention has been attained by providing a method for determining the concentration of an L-amino acid in a culture medium or cultured broth solution which comprises contacting said culture anaerobically with a microbial electrode comprising a fixed or immobilized micro-organism capable of anaerobically decarboxylating said L-amino acid and thereby liberating carbon dioxide into said culture, and a carbon dioxide gas sensitive electrode,
  electrochemically measuring the liberation of carbon dioxide into said culture and thereby
  correspondingly determining the concentration of said L-amino acid in said culture.

A still further object of the invention has been attained by providing a microbial electrode for determining the concentration of a volatile or non-volatile carbon source in a culture medium or cultured broth solution which comprises an oxygen sensitive electrode and a fixed or immobilized micro organism strain capable of aerobically metabolizing said carbon source and thereby consuming oxygen in said solution, said micro-organism being attached to the surface of the diaphragm of said oxygen sensitive electrode and being covered with a membrane thereon.

Still another object of the invention has been attained by providing a microbial electrode for determining the concentration of an L-amino acid in a culture medium or cultured broth solution which comprises a carbon dioxide gas sensitive electrode and a fixed or immobilized microorganism strain capable of anaerobically decarboxylating said L-amino acid and thereby liberating carbon dioxide into said culture, said microorganism being attached to the surface of the diaphragm of said carbon dioxide-sensitive electrode and being covered with a membrane thereon.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8 is a schematic diagram of a determination system employing the microbial electrode of FIG. 7.

FIG. 11 is a simplified elevational section view of a modification of the microbial electrode equipped with a conventional carbon dioxide gas-sensitive electrode indicated in EXAMPLE 3 which is suitable for determination of L-amino acid.

FIG. 12 is a schematic diagram of a determination system employing the microbial electrode of FIG. 11.

Figure 3:
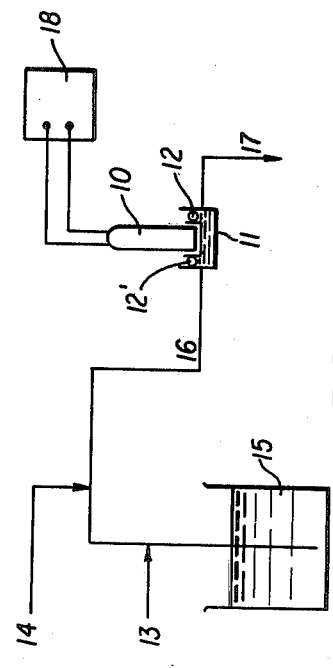
FIG. 3 is a chart indicating the relationship between the time lapse and the concentration of dissolved oxygen (relative indication) when 1.12% (w/v) of aqueous glucose solution is injected into the flow cell at a rate of 0.1 ml/min. with various consecutively changing pulse widths.

DETAILED DESCRIPTION OF THE PREFERRED EMBODIMENTS (1) Method and apparatus for determining carbon source The method for determining a carbon source according to the present invention comprises measuring the rate of current decrease by a microbial electrode which comprises an oxygen-sensitive electrode and a membrane for retaining microorganism cells in an aqueous liquid. The decrease is caused by the consumption of oxygen dissolved in the liquid by fixed microorganisms during the assimilation of the carbon source in the liquid. The concentration of the carbon source can be calculated from the rate of current decrease, by making use of the relationship between the concentration of carbon source and the rate of current decrease.

In this method, the fixed microorganisms are indirectly or closely contacted with the diaphragm membrane of an oxygen-sensitive electrode. The fixed microorganisms and the oxygen-sensitive electrode together form a microbial electrode.

Fixed microorganisms employed according to the present invention are those which are immobilized by trapping microbial intact cells between a diaphragm membrane or the electrode and a dialysis membrane or like solid film, or gas permeable membrane; or they may be dispersed in a continuous solid matrix of a material having the same properties such as collagen and other natural polymers or in certain synthetic resin gels known in themselves.

Dialysis membranes or like solid bodies employed according to the present invention are preferably those which are permeable to $O_2$ and organic compounds in the liquid but impermeable to the entrapped microbial cells. For example, conventional dialysis membranes such as cellophane, acetyl cellulose membrane, and semi-permeable membranes as Milipore filter (Trademark of Milipore Ltd. Co.) and nylon net are preferable. However, when a volatile carbon source is used, a gas-permeable membrane such as porous Teflon, Silicone (Trademark of Shinetsu-Kagaku Co., Inc.), polybutadiene and polyethylene membrane that are permeable only to volatile carbon sources and $O_2$ gas but impermeable to other organic compounds must be employed.

Microorganisms employed according to the present invention are those which are capable of consuming oxygen dissolved in an aqueous liquid in the course of assimilating a carbon source in preference to other organic materials which may be assimilated by the microorganisms. Examples of these are bacteria such as *Pseudomonas fluorescens, Staphylococcus aureus* and *Brevibacterium flavum;* yeast such as *Saccharomyces cerevisae, Tricosporon bracicae,* and *Torulopsis pintropesii.*

When selecting the strain employable for this determination, it is most preferable to use a strain of a microorganism which is useful for the fermentation itself and which has the capability mentioned above.

For example, for determining L-glutamic acid, a strain of *Brevibacterium flavum* ATCC 14067 which is used for L-glutamic acid fermentation is preferably used for the determination of carbon sources such as glucose, fructose, sucrose or acetic acid in the culture medium during L-glutamic acid fermentation.

Microorganisms employed according to the present invention to determine the presence of methanol in a culture medium of SCP fermentation are those which are capable of assimilating methanol as a carbon source and grow rapidly. For example, *Methanomonus methanica, Pseudomonas methylotropha Pseudomonas insuete, Achromobacter methanolophyla* and *Candida parapsilosis* are preferably employed. The microorganism is cultured under aerobic conditions at a temperature in the range from 20° to 37° C. for 10 to 30 hours in a conventional culture medium containing a carbon source, a nitrogen source, a minor nutrient element and inorganic ions. The microbial cells are then harvested by centrifuging the culture broth, washed with water and stored at a low temperature.

The oxygen-sensitive electrode employed according to the present invention can be of any conventional type.

In the following description, reference will be made by way of example to the accompanying drawings.

Figure 1:
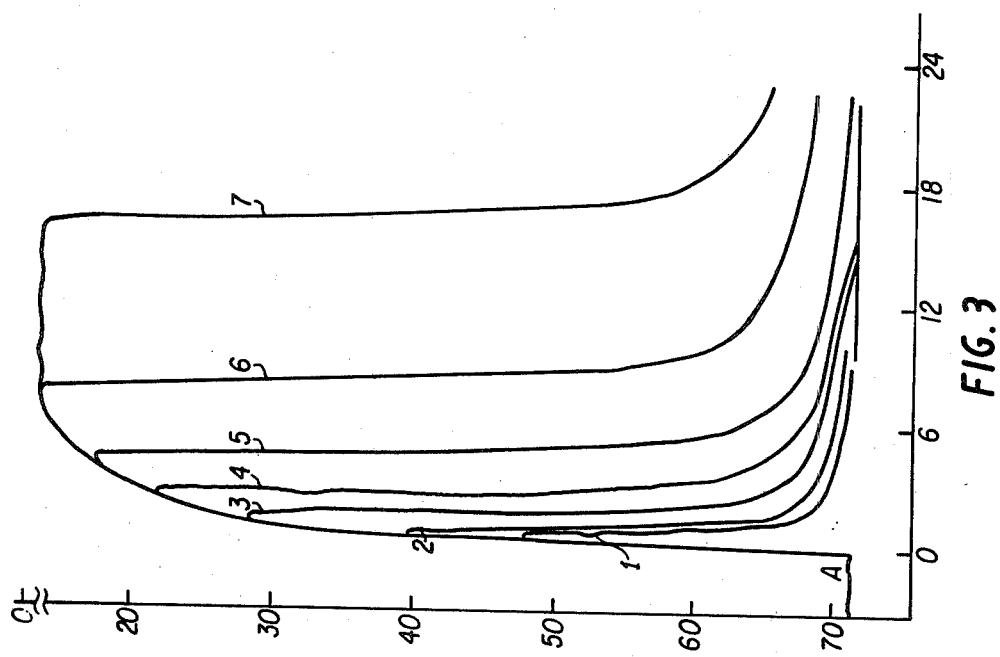
FIG. 1 is a simplified elevational section view of the microbial electrode indicated in EXAMPLE 1 equipped with a conventional oxygen-sensitive electrode which is suitable for determining non-volatile carbon sources.

FIG. 1 shows a microbial electrode 10 formed by smearing intact wet cells of a microorganism on a diaphragm membrane 3 and covering the microbial layer 1 thus formed with a dialysis membrane 2 such as a cellophane membrane to keep the microorganisms in place. The electrode further consists of gold cathode 4 and silver anode 5, rubber ring 6 for fixing membranes to the electrode, electrolyte (KCl) solution 7, lead-in wire 8 and cover 9. In the electrode shown in FIG. 1, the microorganisms may be held between membranes 2 and 3 in a solid carrier, such as a piece of filter paper, containing a definite quantity of intact microbial cells or may be held in a polymer matrix such as collagen and polyacrylamide gel in the form of immobilized microorganisms. This method is preferable since the amount of intact cells used may be easily controlled and the microbial electrodes thus obtained have uniform characteristics.

Figure 2:
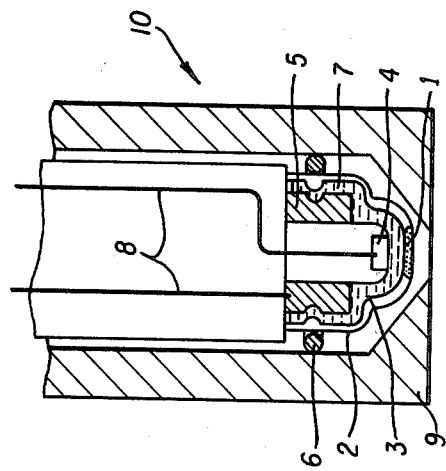
FIG. 2 is a schematic diagram of a determination system employing the microbial electrode of FIG. 1.

An example of a schematic diagram of the continuous determining system of the invention is illustrated in FIG. 2 or FIG. 8.

In FIG. 2, there are shown a microbial electrode 10, flow cell 11, rubber rings for fixing electrodes 12, 12', recorder 18, delivery inlet for sample solution with carrier solution 16, outlet for waste solution 17, inlet for blow-in air 13, delivery for sample 14, and reservoir for carrier solution 15 which are all self-explanatory.

In FIG. 8, distilled water or buffered water saturated with dissolved oxygen is fed into the flow cell 11 at a constant flow rate during the determination with the current of the electrode 10 recorded. After the current has attained a constant value (referred to as the "base current" or "base line"), the sample solution (culture medium or cultured broth) from automatic sampler 14 is directly injected into the system by the auto sampler at a constant flow rate at a constant interval, diluted by flowing water or buffered water, saturated with dissolved oxygen, and put into the cell 11 and stirred by the magnetic stirrer 20. The temperature of the flow cell 11 is maintained by the jacket 19 at a constant temperature in the range from 15° to 30° C. during the determination. When the sample solution is introduced into the flow cell 11 and contacted with the microbial electrode 10, the current of the electrode which is visually recorded on the recorder 18 decreases markedly with time, until it reaches a steady state, as illustrated in FIG. 3. The time to reach a steady state is within 10 to 15 minutes. The decrease in current is caused by an uptake of dissolved oxygen by the fixed microorganism of the electrode in the course of assimilating the carbon source from the sample solution. The rate of the current decrease and the decrease in current in a steady state are dependent upon each other and are therefore proportional to the concentration of the carbon source. Therefore, the concentration of the carbon source can be calculated from the rate of current decrease or decrease in current in a steady state by virtue of the linear relationship between them.

As the microorganisms of the electrode can assimilate the carbon source rapidly, the time of sample injection is as short as 1 to 10 minutes. As to the time of contacting the microorganisms with the sample solution, it is desirable for the time to be as short as possible since if the microorganisms remain in contact with the sample solution for an extended time, other organic compounds contained in the sample solution such as amino acid may be assimilated by the microorganisms to cause an undesirable uptake of dissolved oxygen.

Since the rate of current decrease is influenced by the pH and temperature, it is necessary to perform the determination procedure at a constant temperature ranging from 15° to 40° C. and a pH ranging from 3.0–8.5. When a volatile carbon source such as acetic acid in a culture medium is determined, the pH of the aqueous liquid in the flow cell must be kept sufficiently below the pK value of acetic acid (4.75 at 30° C.) since most acetic acid molecules exist in the form of acetate ions above the pK values where they cannot pass through the gas permeable membrane.

The rate of current decrease is also slightly influenced by the kind of carbon source. Therefore, it is desirable to determine the relationship between the carbon source to be determined and the rate of current decrease prior to the determination.

The method of the present invention is not affected by other organic compounds and inorganic ions coexisting in the culture medium. For example, L-amino acids such as L-glutamic acid, L-lysine, L-aspartic acid, vitamins, base nucleotides, proteins (enzyme), peptides, polysaccharides, antifoaming agent and surface-active agents do not affect the method of the present invention.

The method of the present invention is more preferable than the conventional method of determining the reducing power of the carbon source, since the concentration of the saccharide in a culture medium of L-glutamic fermentation can be determined exactly. In prior art methods of determining reducing power (such as the Park-Johnson method) the concentration cannot be determined exactly, since a considerable amount of reducing impurities are usually contained in a culture medium of glutamic acid fermentation.

(2) Method and apparatus for determining L-Amino Acid

Figure 14:
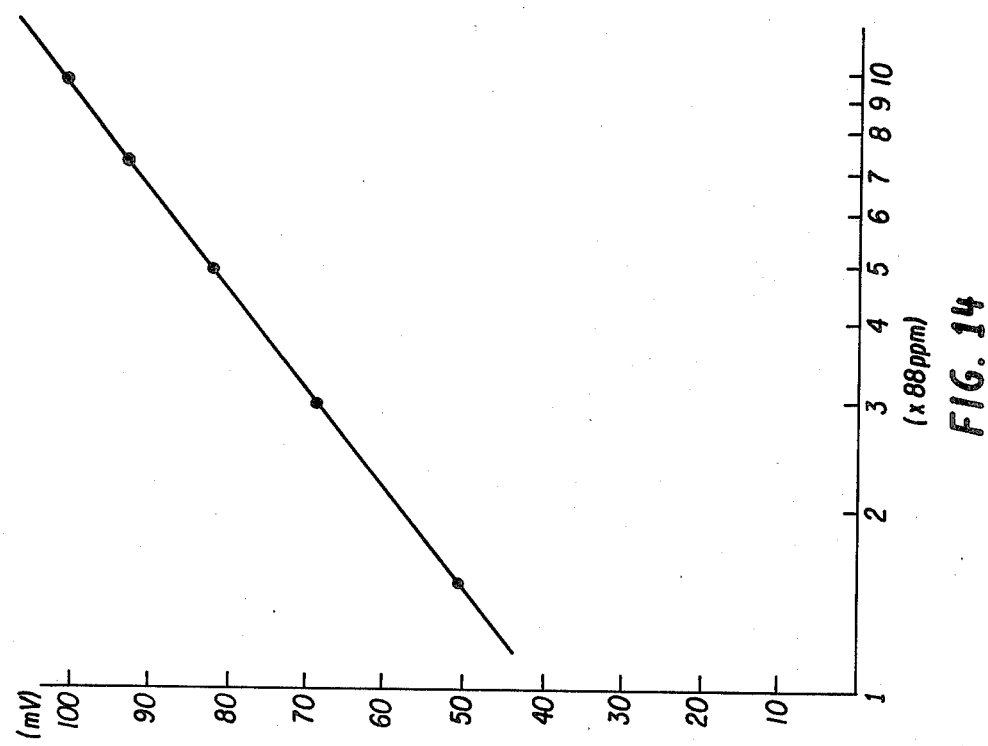
FIG. 14 is a chart showing comformity of the results of the determination of FIG. 13 with the theoretical line calculated by the Nernst's equation.

According to the present invention there is provided a method for determining L-amino acid in a culture medium or fermentation broth by means of a microbial electrode. The method comprises measuring the electromotive force (E.M.F.) of a $CO_2$ gas-sensitive electrode in an aqueous liquid, where E.M.F. is produced in accordance with the reaction (I) performed under anaerobic conditions by the fixed microorganisms of the microbial electrode. The calculation of the concentration of L-amino acid is carried out by using the relationship between the concentration C (C=concentration of L-amino acid) and the E.M.F. as shown in FIG. 14 and which is given by Nernst's equation:

$$E = E_o - (2.303RT/F) \log C \qquad \text{II}$$

In this equation $E_o$ is an unsymmetric potential difference, R is the gas constant, T is the absolute temperature and F is Faraday's constant.

The microorganisms employed according to the present invention are those which contain and show L-amino acid decarboxylase activity. For example, microorganisms having L-glutamic acid decarboxylase activity such as *Escherichia coli* ATCC 8739, *Citrobacter freundii* ATCC 10787, *Clostridium welchii* ATCC 13124, *Rhodotorula glutinis* IFO 0413 are employed to determine L-glutamic acid. Those haing L-lysine decarboxylase activity such as *Escherichia coli* ATCC 23226, *Bacterium cadaveris* ATCC 9760, *Streptococcus faecalis* ATCC 12984, *Pseudomonus saccharophia* ATCC 15946, *Bacillus subtilis* ATCC 15037, *Lactobacillus casei* ATCC 7469 are preferably employed to determine L-lysine.

To determine L-phenylalanine and L-arginine, microorganisms having L-phenylalanine or L-arginine decarboxylase activity such as *Streptococcus faecalis* ATCC 8043, *Escherichia coli* ATCC 10787 are preferably used.

These microorganisms may be cultured under aerobic or anaerobic conditions in a conventional manner and the microbial cells obtained can be used directly as a form of microbial electrode.

According to the methods of the present invention, other than intact cells, freeze dried cells or microbial cells which are treated with organic solvent and/or surface-active agents, are also preferably employed. As an organic solvent for this purpose, acetone, ethanol, methanol, isopropanol, n-propanol, toluene and ether may be used.

Surface-active agents employed according to the present invention are those which have strong osmotic power but do not spoil the enzyme activity. For example, cetyltrimethyl ammonium bromide, cetylpiridinium bromide, sodium lauryl sulfate, polyethylene alkyl ether, and alkyl betaine are preferably used. For example, the microbial cells which are cultured, harvested and washed with water are immersed in the aqueous liquid containing a substantial amount of surface-active agent and/or treated with organic solvent and then dried under a low temperature. The microbial cells thus obtained contain $10^6$/g of living cells and are preferably used for a term as long as 2 years.

The microbial electrode employed according to the present invention to determine L-amino acid is formed by fixing the microorganisms described above to a $CO_2$ gas-sensitive electrode in a similar manner than that which was previously described in the method of forming the microbial electrode used for the determination of a carbon source.

The $CO_2$ gas-sensitive electrode employed according to the present invention can be of any conventional type.

FIG. 11 shows a microbial electrode comprising a diaphragm 3 of the electrode such as silicone membrane to which the microorganisms are fixed, the microorganism layer 1, spacer 1' such as a piece of filter paper, dialysis membrane or like solid body 2 such as Milipore filter (Trademark of Miliporo Ltd, Co.) membrane and nylon net, pH electrode 4' and an internal electrolyte solution 7 such as an aqueous liquid containing $NaHCO_3$ and NaCl.

The schematic diagram of the method of the invention is illustrated in FIG. 12 which is similar to that illustrated in FIG. 2 except that $N_2$ gas is injected into the determining system from injecting nozzle 13' instead of air or $O_2$ gas.

In FIG. 12 there is shown a microbial electrode 10, a flow cell 11, rubber stopper 12, 12', $N_2$ gas-injecting nozzle 13', injecting nozzles of carrier solution 15, sample solution 14, pH meter or ion meter 18' and a recorder 18.

A carrier solution having pH-values of 3.5 to 5.5 and $N_2$ gas are injected into the determination system from nozzles 14 and 15 at a constant flow rate respectively, and the temperature in the flow cell is maintained at a constant temperature ranging from 20° to 40° C. during the determination.

The electromotive force of the electrode is visually recorded by a recorder (Base line).

After the base line has attained a constant value, the sample solution (a culture medium, cultured broth or diluted solution thereof) is injected into the determination system from nozzle 14 for 0.5 to 3 minutes at a constant flow rate at a regular interval time, diluted with the circulating carrier solution so that the concentration of L-amino acid in the flow cell may be from $10^{-4}$ to $10^{-1}$M, and fed into the flow cell.

In the flow cell, L-amino acid in the sample solution is decomposed by the fixed microorganisms of the electrode and $CO_2$ gas is produced according to reaction (I). The $CO_2$ produced permeates through a diaphragm of the electrode and changes the pH of the interval electrolyte solution 7. The pH change is determined by the pH meter or ion meter 18' and recorded by the recorder 18.

The concentration of L-amino acid in the sample solution may be calculated from Nernst's equation (II) previously described.

As a carrier solution employed according to the present invention, a buffer solution 15 containing an organic acid such as citric acid, fumaric acid or succinic acid, or pyridine-HCl buffer solution is preferable. Among these, the pyridine-HCl buffer solution containing NaCl and $KH_2PO_4$ (0.5 g/dl) is most preferably used.

According to the present invention, the reaction (I) in the flow cell must be carried under anaerobic conditions. If reaction (I) is carried out aerobically, the fixed microorganisms assimilate nutrient materials derived from culture medium or cultured broth such as saccharide and amino acids; i.e. respiration of the microorganisms occurs and a large amount of $CO_2$ gas which is produced by the microbial respiration itself makes the determination of L-amino acid impossible.

It has now been found that the $CO_2$ gas production by action of the living microorganisms is completely depressed by carrying out the reaction (I) under an anaerobic condition, where the reaction (I) by the living microorganisms proceeds quantitatively enough to be used for the determination of the objective L-amino acid.

An anaerobic condition under which the reaction (I) is carried out according to the present invention is that under which there is no dissolved oxygen contained in a reaction system of the fixed microorganism. The anaerobic condition is maintained not only by injection of $N_2$ gas but also other inert gases such as argon or helium into a carrier solution containing no dissolved oxygen.

It would appear at first that the method of the present invention may be affected by the impurities derived from the culture medium such as saccharides, organic acid and other amino acids since the method employs living microorganisms. However, the method of the present invention is not affected by those impurities. For example, the method for the determination of L-lysine using a microbial electrode comprising fixed micro-organisms of *Escherichia coli* ATCC 23226 and a $CO_2$ gas-sensitive electrode is not affected by other amino acids as shown in the following Table.

| Amino acid | Electromotive force (E.M.F.) |
|---|---|
| L-lysine | 100.0 |
| Glycine | 1.3 |
| L-alanine | 1.3 |
| L-valine | 1.1 |
| L-leucine | 1.2 |
| L-tyrosine | 7.6 |
| L-tryptophan | 7.4 |
| L-glutamic acid | 3.7 |
| L-proline | 1.3 |

In this experiment, each concentration of L-amino acid in the sample solution is equal to that of L-lysine. The Table shows that there is no amino acid which has E.M.F. values more than 10% of L-lysine.

Other amino acids which are not shown in the above Table and other organic compounds usually contained in a cultured broth are also determined similarly.

It is found that the method of determining L-lysine is not affected by L-serine, L-threonine, L-cysteine, L-cystine, L-methionine, L-aspartic acid, L-glutamine, L-phenylalanine, L-asparagine, L-histidine, L-arginine, L-ornitine HCl, L-citrulline, L-isoleucine, D,L-lactic acid, tartaric acid, α-ketoglutaric acid, succinic acid, malic acid, fumaric acid, citric acid, glucose, and urea.

Compared with the method of the present invention, a common acidic ninhydrin method for determination of L-lysine is affected by other amino acid such as L-cysteine as shown in the following Table.

| Amino acid | |
|---|---|
| L-lysine | 100% |
| L-cysteine | 8% |
| L-cystine | 3% |
| L-tyrosine | 11% |
| L-histidine | 4% |
| L-proline | 17% |
| L-ornitine HCl | 8% |

It is apparent from these results that the method of the present invention is superior to a common acidic ninhydrin method in selectivity.

As described above in detail, an extremely rapid, simple and continuous determination of a carbon source and L-amino acid in a culture medium or cultured broth can be achieved with precision and reproducibility. This new method for determination will be useful for on-line measurement of a carbon source and L-amino acid in a culture medium or cultured broth during fermentation and is especially necessary for feeding methods.

Having generally described this invention, a further understanding can be obtained by reference to certain specific examples which are provided herein for purpose of illustration only and are not intended to be limiting unless otherwise specified. In the examples, percent represents percent w/v.

EXAMPLE 1

*Brevibacterium flavum* ATCC 14067, grown on a nutrient agar slant, was cultivated with shaking in a nutrient broth supplemented with 1% glucose at 30° C. for 24 hours. A 25 ml portion of a medium (total volume: 100 ml) containing the components given in Tab. 1 was added to a 500 ml-flask, sterilized at 120° C. for 15 minutes and cooled. Each flask was supplemented with 0.5 ml of 30% urea solution separately sterilized.

TABLE 1

| Composition of medium (pH 6.0) | |
|---|---|
| Component | Concentration |
| Glucose | 4.0 g/dl |
| $K_2HPO_4$ | 0.1 g/dl |
| $MgSO_4.7H_2O$ | 0.1 g/dl |
| $FeSO_4.7H_2O$ | 2 ppm |
| $MnSO_4.4H_2O$ | 2 ppm |
| Soy bean extract | 24 ml/l |
| Thiamine HCl | 100 mcg/l |
| Urea | 0.6 g/dl |

The medium was inoculated with 0.5 ml of the seed culture and incubated with shaking at 30° C. for 24 hours. Cells were harvested by centrifuging 30 ml of the cultured broth and washed with water 3 times to give 4 ml of cell paste (1). A microbial electrode (10) shown in FIG. 1 was obtained by spreading a loop of the cell paste over a Teflon membrane (3) of a polarograph-type dissolved oxygen-sensitive electrode (Beckman Model 777), covering the paste with cellophane membrane (2) and fixing the upper part with a rubber band (6). The electrode (10) was inserted into a flow cell (11) through a rubber packing (12, 12') to give a 0.5 ml-flow cell. A continuous measuring system shown in FIG. 2 was assembled with the flow cell.

Figure 4:
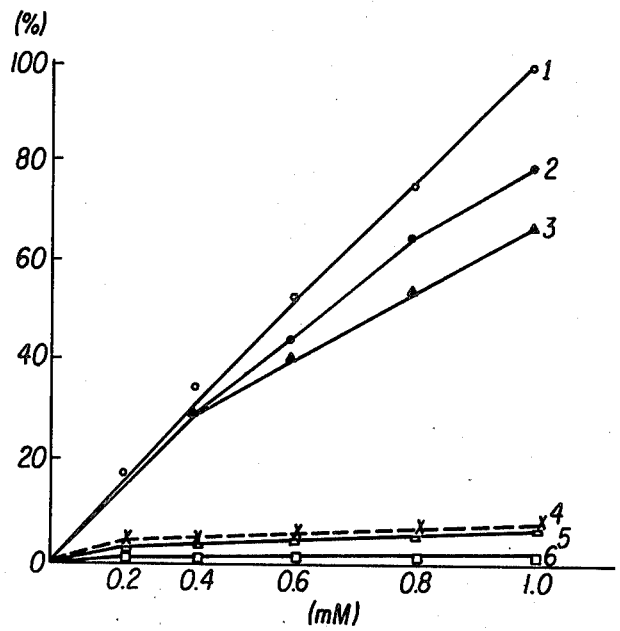
FIG. 4 is a chart which indicates the relationship between the concentration of various carbon sources (1. glucose, 2. fructose, 3. sucrose, 4. L-glutamic acid, 5. lactose, 6. trehalose) and the concentration of dissolved oxygen (relative indication) when injected with various concentrations of various carbon sources into the flow cell at a pulse width of 30 seconds, at an interval of 5 minutes.

In FIG. 2 the numbers represent the followings, respectively:

(10)—Microbial electrode
(11)—Flow cell (12, 12')—Rubber packing
(18)—Recorder
(16)—Pipe for carrier fluid containing sample
(13)—Input of air
(14)—Input of sample
(15)—Carrier fluid reservoir For measurement, water was flowed at a flow rate of 5 ml/min while blowing air into it at a rate of 6 to 10 l/h. Thus, the oxygen saturated water runs in the flow cell as a carrier fluid. The inside temperature of the flow cell was adjusted to 30° C. After the electric current of the microbial electrode was stabilized (after obtaining a stable base-line), 1.12% glucose solution was injected at a rate of 0.1 ml/min. The electric current of the electrode was recorded varying the injection time (width of pulse) from 0.5 minutes to 16 minutes. The results are shown in FIG. 3 in which the axis of abscissa shows time (minutes) and the axis of ordinate shows the amount of dissolved oxygen (relative value). The relative value O means that dissolved oxygen is O. "A" represents a base-line (the value of oxygen-saturated water). In this figure 1, 2, 3, 4, 5, 6 and 7 show pulse widths of 0.25, 0.5, 1.0, 2.0, 4.0, 6.0 and 16 minutes, respectively. The electric current of the microbial electrode began to decrease a few seconds after a sample was injected and reached a constant level after about 10 minutes (steady state current). Then, glucose was injected with various concentration at an interval of 5 minutes with pulse width of 30 seconds, whereby the relationship between the height of the peak and the concentration was examined. Similar tests were carried out with fructose, sucrose, glutamic acid, trehalose and lactose. The results are shown in FIG. 4 in which the axis of abscissa represents the concentration in the flow cell and the axis of ordinate represents the peak height calculated based on glucose (the peak height of 1 mM glucose is 100%). Curves 1 to 6 were obtained with the following sugars, respectively:

1:Glucose
2:Fructose
3:Sucrose
4:L-glutamic acid
5:Lactose
6:Trehalose

Figure 5:
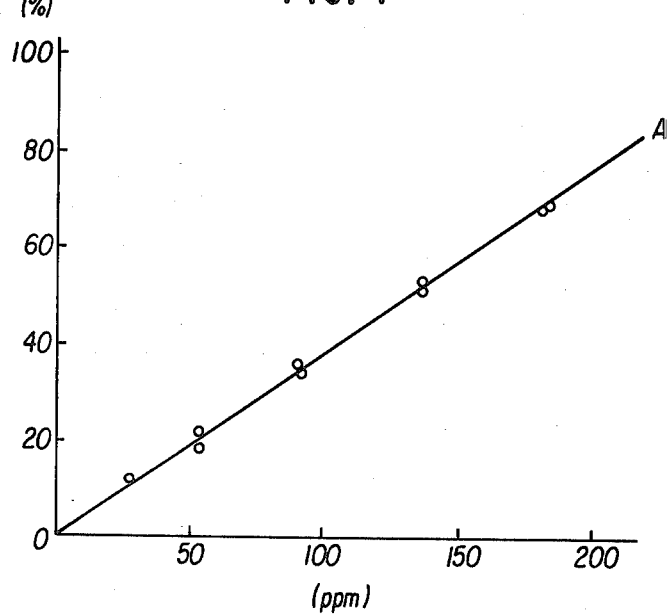
FIG. 5 is a chart showing the conformity of the result of the determination (white circles) of the concentration of a cane molasses aqueous solution by the method of this invention with the theoretical line (line A) which is prepared and based on the standard line of FIG. 4.

Cane molasses (abbreviated as CM) of 0.9% sugar content was diluted. A similar test was also performed with the diluted solution with a pulse width of 30 seconds, whereby the relationship between the sugar concentration and the peak height was examined. FIG. 5 shows the results. In the figure, the open circles represent the results which are in good agreement with the theoretical value shown by the solid line A which was obtained by calculation (simple addition) based on the sugar composition (sucrose:glucose:fructose 60:20:20) of CM and on the standard curve in FIG. 4.

Residual sugar concentration of the cultured broth was measured with a pulse width of 30 seconds and calculated based on the CM-standard curve (theoretical value) in a glutamic acid fermentation that was accomplished with CM as the starting material Tab. 2 shows the results.

TABLE 2

| | Residual sugar concentration of fermentation broth | | |
|---|---|---|---|
| | | Residual sugar (g/dl) | |
| Time (hour) | L-glutamic acid production (g/dl) | Microbial electrode | Lehman Schule method |
| 10 | | 0.75 | 1.9 |
| 20 | | 0.35 | 1.8 |
| 30 | 7.5 | 0.16 | 1.6 |

On the 30th hour of the fermentation, the method according to the present invention provided a residual sugar concentration of 0.16 g/dl. This was one tenth less than 1.6 g/dl which was the value obtained according to the conventional method of Lehman Schule. The residual sugar concentration of the fermentation broth was also assayed by paper chromatography. There was almost no sugar that might be assimilated by the microorganism. Therefore, the results obtained according to the conventional method only show the reducing activity of reducible compounds. On the contrary, the method according to the present invention can provide an accurate amount of residual sugar without being influenced by other reducible compounds and by glutamic acid that coexists in the fermentation broth at a high concentration.

Stability of the microbial electrode was tested by feeding 0.75% aqueous glucose solution automatically with a pulse width of 30 sec (temperature:30° C.) and at a 30 minutes interval into the system in FIG. 2 which was assembled with the microbial electrode constructed according to FIG. 1. The results are given in FIG. 6, which shows that no change was observed during a continuous operation for 2 weeks.

EXAMPLE 2

Figure 7:
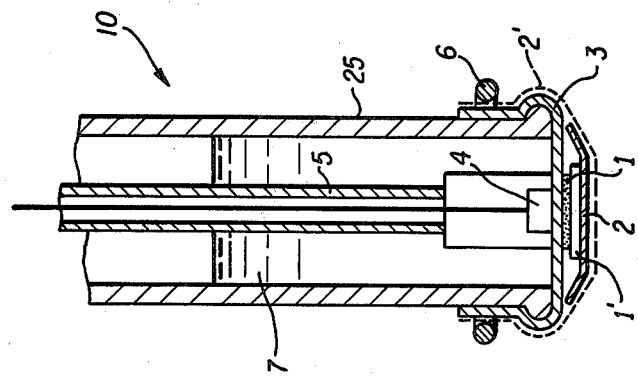
FIG. 7 is a simplified elevational section view of a modification of the microbial electrode equipped with a conventional oxygen-sensitive electrode indicated in EXAMPLE 2 which is suitable for the determination of a volatile carbon source.
Figure 6:
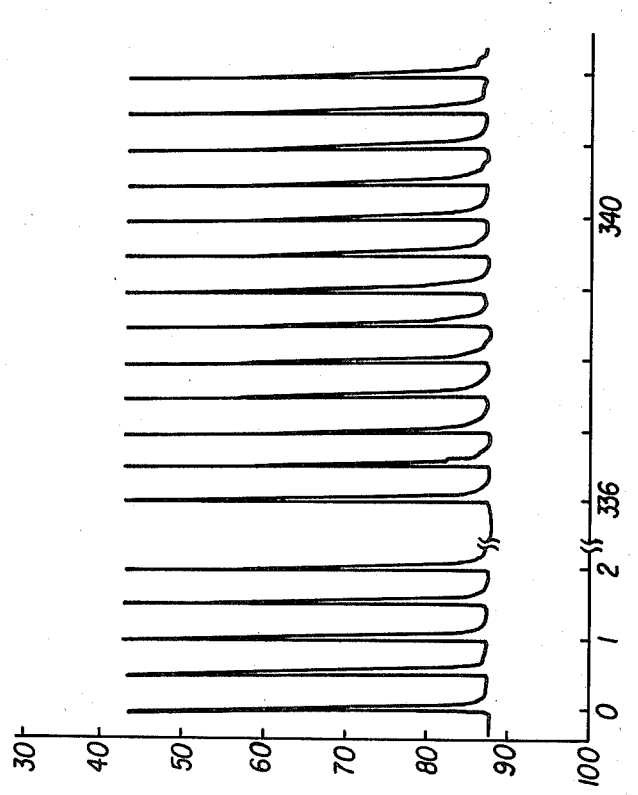
FIG. 6 is a chart indicating the stability of the microbial electrode of FIG. 1 when injecting 0.75% (w/v) of glucose aqueous solution into the system of FIG. 2 at the pulse width of 30 seconds (30° C.) at an interval of 30 minutes (the axis of abscissa indicating hours).

*Trichosporon brassicae* CBS 6382 was cultivated on an agar slant midium containing 0.3 g/dl malt extract, 0.3 g/dl yeast extract, 0.3 g/dl peptone, 1.0 g/dl glucose and 2.0 g/dl agar. The microbial cells grown on the slant were harvested and 0.3 of the wet cells were suspended into 5 ml of water. The cell suspension (3 ml) was dripped on a porous acetyl cellulose membrane (Type HA, pore size: 0.45 micron, diameter: 47 mm and thickness: 150 micron, Milipore Ltd.). Then a microbial electrode as illustrated in FIG. 7 was assembled by the same manner as described in EXAMPLE 1, which was another type of microbial electrode according to the present invention. The porous acetyl cellulose membrane (1') retaining the microbial cells (1) was cut into a circle (diameter: 14 mm) and fixed on the surface of a Teflon membrane (3) (thickness: 50 micron) of an oxygen-sensitive electrode (Model C-321, Denki Kagaku Keiki Co.) which was covered with a gas permeable membrane (2) (porous Teflon membrane Type PH, pore size: 0.5 micron, Milipore Ltd.) or a silicone rubber membrane (Type D 606, Radiometer Co.) and then with a Nylon net (2'). Therefore, the microorganisms were trapped between the two membranes, thus, a microbial electrode (10) was assembled. The electrode further involved an aluminum anode (5), saturated potassium chloride electrolyte solution (7), an insulator (25), a platinum cathode (4) and a rubber ring (6) for fixing the membranes.

Furthermore, the gas permeable Teflon membrane was placed on the surface of the electrode and covered with a Nylon net. These membranes were fastened with rubber rings as illustrated in FIG. 7.

FIG. 8 shows a schematic diagram of the system. The system consisted of a microbial electrode (10), a jacket (19), a flow cell (11) (diameter: 3 cm, height: 2.7 cm, volume: 19 ml, liquid volume: 3 ml), a magnetic stirrer (1000 r.p.m.) (20). As a pump (21), a peristaltic pump (Model I, Technicon) was used. And as an automatic sampler (14') and a current recorder (18), Model SC-160 FA (Toyo Kagaku Sangyo Co.) and Model ERB-6-10 or Model LER-12A (Yokogawa Electric Works Co.) were employed, respectively.

The temperature of the flow cell (11) was maintained at 30±0.1° C. by warm water (23) passed through the jacket (19). Buffered tap water (15) was adjusted to pH 3 with 0.1 $NH_2SO_4$ and saturated with air (13). Then it was transferred to the flow cell (11) at a rate of 1.4 ml/min together with 200 ml/min of air (13). When the output current of the microbial electrode reached a constant value, a sample was injected into the system at a rate of 0.8 ml/min for 3, 10 or 15 minutes intervals.

Figure 9:
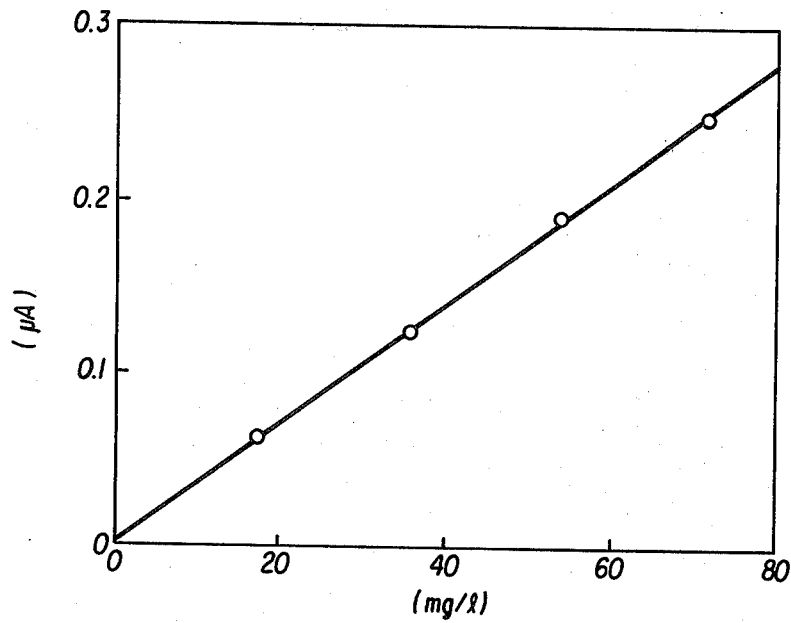
FIG. 9 is a chart showing the relationship of the concentration of acetic acid (mg/l) and the current decrease ($\mu A$) indicated in EXAMPLE 2.

FIG. 9 shows calibration curves of the microbial electrode, in which the axis of abscissa represents acetic acid concentration (mg/l) and the axis of ordinate represents current decrease (μA). A linear relationship was observed between the current decrease and the concentration of acetic acid below 72 mg/l by the pulse method. The minimum concentration for determination was 5 mg of acetic acid per liter. The reproducibility of the current difference was examined using the same sample. The current difference was reproducible within ±6% of the relative error when the sample containing 54 mg/l of acetic acid was employed. The standard deviation was 1.6 mg/l in 20 experiments.

The selectivity of the microbial electrode for acetic acid was examined. Tab. 3 shows the selectivity of the electrode. The sensor did not respond to volatile compounds such as formic acid and methyl alcohol and non-volatile nutrients for microorganisms such as glucose and ions. As the microbial electrode is covered with a gas permeable membrane, only volatile compounds can penetrate through the membrane. Response to organic compound depends on the assimilability of the immobilized microorganisms. Acetic acid utilizing yeast, *Trichosporon brassicae*, did not utilize formic acid and methyl alcohol, but utilized propionic acid, n-butyric acid and ethyl alcohol. Therefore, existence of such compounds prevent the determination of acetic acid. However, those compounds are generally not so much in fermentation broths as they may affect the determination.

TABLE 3

| | Response of the microbial electrode sensor to various compounds | |
|---|---|---|
| Compounds | Concentration* | Current decrease (micro A)** |
| Acetic acid | 100 mg/l | 0.18 |
| Formic acid | 100 mg/l | 0 |
| Propionic acid | 100 mg/l | 0.17 |
| n-Butyric acid | 100 mg/l | 0.21 |
| Lactic acid | 100 mg/l | 0 |
| Succinic acid | 100 mg/l | 0 |
| Tartaric acid | 100 mg/l | 0 |
| Methyl Alcohol | 40 mg/l | 0 |
| Ethyl Alcohol | 40 mg/l | 0.21 |
| Glucose | 10 g/l | 0 |
| $KH_2PO_4$ | 50 g/l | 0 |

*Original concentration (diluted 2.8 times in the flow cell).
**Injection time interval: 15 min.

Figure 10:
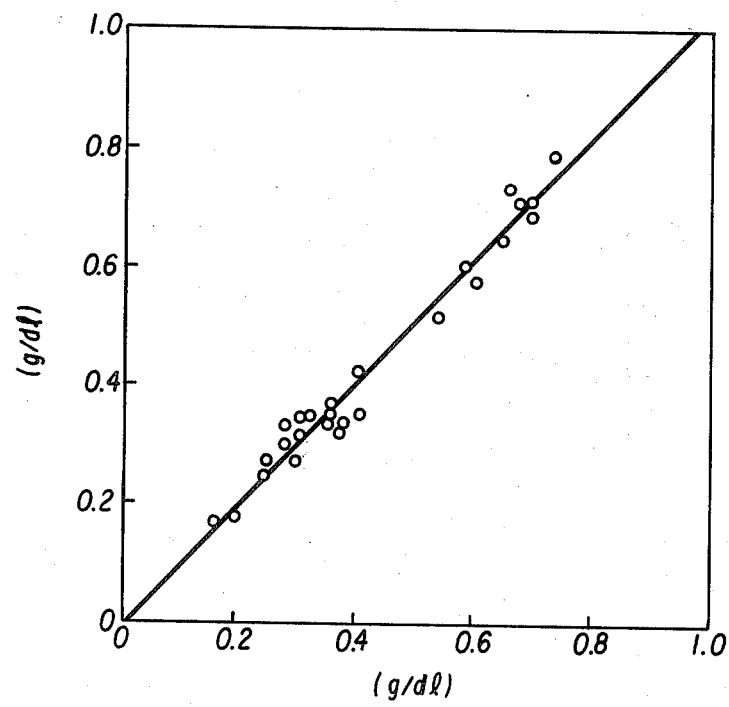
FIG. 10 is a chart showing the conformity of the results of the present method (the axis of abscissa) with that of gas chromatography (axis of ordinate) when determining a sample of acetic acid aqueous solution.

The microbial electrode for acetic acid was applied to a fermentation broth of glutamic acid. The glutamic acid fermentation broth (acetic acid was used as carbon source) was diluted (dilution time of sample was 170 times) and injected into the measuring system automatically (interval time of injection was 10 minutes). The concentration of acetic acid was determined by the microbial electrode and by gas chromatography. As shown in FIG. 10 in which the axis of abscissa shows the result by microbial electrode (g/dl) and ordinate shows that by gas chromatography (g/dl), satisfactory consistent results were obtained between them. Correlation coefficient was 1.04 with 26 experiments. Whole cells in the broth did not affect the electrochemical determination of acetic acid. The reusability of the microbial electrode for acetic acid was examined. Acetic acid solutions (from 18 mg/l to 72 mg/l) were used for long term stability test of the electrode. The current output of the electrode was almost constant for more than 3 weeks and 1500 assays. Therefore, the yeasts in the electrode were living for long time. The microbial electrode can be used for long time for the assay of acetic acid. In conclusion, the microbial electrode sensor appears quite promising and very attractive for the determination of acetic acid in a fermentation broth.

EXAMPLE 3

*Escherichia coli* ATCC 8739 was grown at 30° C. with shaking in a medium containing the components shown in Tab. 4.

After 20 hours, 50 ml of the cultured broth was centrifuged to harvest cells. The wet cells were washed well with 50 ml of 0.1 MKCl and freeze-dried to give 0.6 f of lyophilized cells.

TABLE 4

| Composition of medium (pH 7.0) | |
|---|---|
| Component | Content |
| Glucose | 1.0 g/dl |
| Casamino acids | 1.0 g/dl |
| $KH_2PO_4$ | 0.5 g/dl |
| Glutamic acid (Na salt) | 0.2 g/dl |
| Yeast extract | 0.2 g/dl |
| Antifoam (Toshiba Silicone) | 0.1 ml/dl |

FIG. 11 describes this experiment.

The lyophilized cells (1) (5 mg) were suspended into a small amount of water to obtain a cell paste, which was spread over a Nylon net (1') (diameter: 10 min). It was fixed to a silicone membrane (3) of a carbon dioxide gas-sensitive electrode (4') (Model E 5037, Radiometer Co., Denmark) with a cellophane membrane (2) as illustrated in FIG. 11, in which (7) represents an electrolyte solution of $NaHCO_3$-NaCl mixtures.

Figure 13:
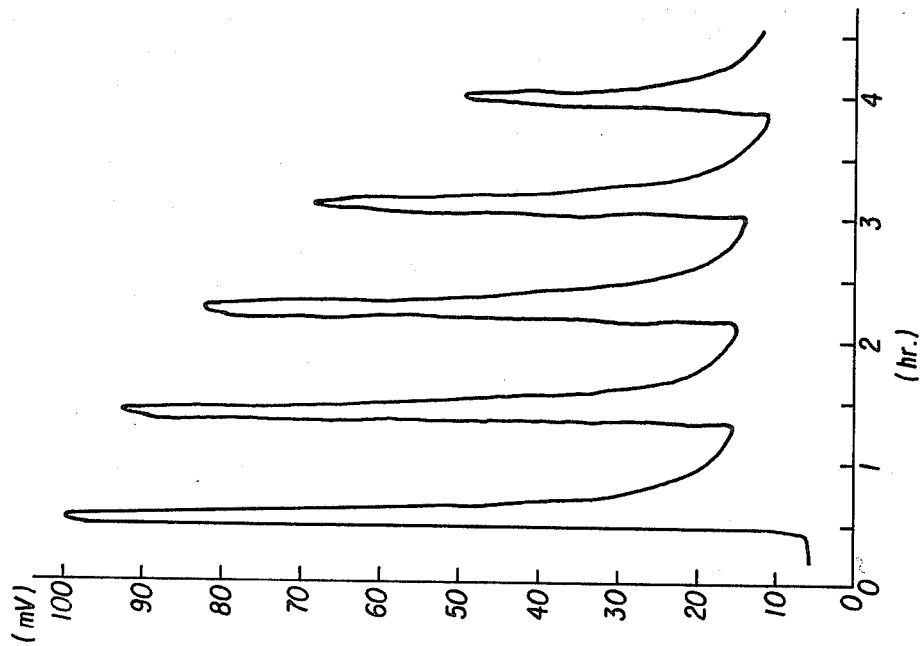
FIG. 13 is a chart indicating the relationship between the electromotive force (in mV) and the concentration of L-glutamic acid aqueous solution when consecutively injecting various concentrations of the acid at the rate of 1 ml/min. with a pulse width of 3 minutes into the flow cell of FIG. 12.

The microbial carbon dioxide electrode (10) was inserted into a flow cell (11) (volume: 0.5 ml) through a rubber packing (12) (12') and a measuring system was assembled as shown in FIG. 12. The following elements are shown in FIG. 12:

(13')—Input of $N_2$ gas
(14)—Input of sample
(15)—Input of carrier buffer solution
(18)—Recorder
(18')—Output voltage meter As a carrier fluid, 0.1 M pyridine-hydrochloric acid buffer solution, pH 4.4 (containing 0.5 g/dl NaCl and 0.5 g/dl $KH_2PO_4$) was fed from (15) at a flow rate of 5 ml/min and $N_2$ gas also brought into the flow cell from (13') at a flow rate of 1 l/min, and then the output voltage was recorded with a recorder (18) (base-line). During the measurement, the temperature inside the flow cell was maintained at 30° C. After 1 hour, 465 ppm aqueous glutamic acid solution and its diluted ones were successively injected from (14) at a rate of 1 ml/min with a pulse width of 3 minutes. The samples were diluted with the buffer solution and flowed into the flow cell, whereby the microbial electrode began to respond within a few seconds. The response reached a saturation level after 3 minutes and the peaks as illustrated in FIG. 13 were obtained by the recorder. In FIG. 13, the axis of ordinate and abscissa represent output voltage (mV) and time (hour), respectively. There was a relationship shown in FIG. 14 between the height of the peak (ordinate) in FIG. 14 and the common logarithm of the concentration of glutamic acid (log C, abscissas) in the flow cell. The linear response curve obtained had a slope of 60 mV/pC$_{Glu}$, which was in agreement with coefficient of Nernst's term in Equation (II) (theoretical value: 60.16 mV).

Brevibacterium lactofermentum ATCC 13896 was cultivated with aeration and agitation at 30° C. in a medium containing the components shown in Tab. 5.

TABLE 5

| Composition of medium | |
|---|---|
| Component | Content |
| Glucose | 6.0 g/dl |
| KH$_2$PO$_4$ | 0.2 g/dl |
| MgSO$_4$ 7H$_2$O | 0.08 g/dl |
| FeSO$_4$ 7H$_2$O | 0.002 g/dl |
| Soy bean extract | 0.1 ml/dl |
| Biotin | 5 mcg/l |
| Vitamin B$_1$ Na-salt | 200 mcg/l |
| Antifoam (Toshiba silicone) | 0.01 ml/dl |

The resulted cultured broth was diluted 100-times, which was Sample A. To the sample were added various amounts of L-glutamic acid of reagent grade, which were Sample B, C and D, respectively. The L-glutamic acid concentration of the sample was calculated according to Equation (II) from the height of the peak obtained by the system shown in FIG. 12. The results are given in Tab. 6. All values obtained by the method according to the present invention coincided with those obtained by the conventional enzymatic method (autoanalyzer method).

TABLE 6

| Assay of L-glutamic acid in cultured broth | | |
|---|---|---|
| | Concentration of L-glutamic acid (g/dl) | |
| Sample | Method according to the present invention | Autoanalyzer method (Conventional method) |
| A | 1.74 | 1.70 |
| B | 2.70 | 2.68 |
| C | 4.16 | 4.18 |
| D | 6.10 | 6.18 |

EXAMPLE 4

The wet cells of E. coli obtained in EXAMPLE 3 were washed twice with 0.1 M KCl and suspended into 5 ml of water. To the suspension was added dropwise 50 ml of acetone at room temperature. The mixture was stirred for 5 to 10 minutes and centrifuged under cooling. The cell cake was washed twice with acetone, once with ether and dried in a vacuum desiccator to obtain 0.6 g of acetone-ether-treated cells.

Said acetone-ether-treated cells (1-2 mg) were suspended into a small amount of water to be paste, which was spreaded over a nylon mesh (diameter: 10 mm). The mesh was fixed on a silicone membrane (3) of a dissolved carbon dioxide gas-sensitive electrode (Model E 5036, Radiometer Co., Denmark) with a cellophane membrane (2) to obtain a microbial electrode (10) as illustrated in FIG. 11.

Concentration of L-glutamic acid was assayed with the microbial electrode by the same method as described in EXAMPLE 3. The results were as same as what are shown in Tab. 6. The value of each sample was in good agreement with one obtained by the conventional autoanalyzer method in which the enzyme from pumpkin was used.

EXAMPLE 5

Rhodotorula glutinis IFO 0413 was grown in a flask with shaking at 30° C. for 48 hours in a medium containing the components as shown in Tab. 7.

TABLE 7

| Composition of medium (pH 6.3) | |
|---|---|
| Component | Content (g/dl) |
| Glucose | 1.0 |
| Peptone | 0.3 |
| Malt extract | 0.3 |
| Yeast extract | 0.3 |
| Sodium L-glutamate | 0.2 |

Wet cells harvested by centrifuging 50 ml of the cultured broth were washed twice with 0.1 M KCl and suspended into 50 ml of an aqueous solution containing 20 mg of cetyltrimethylammonium bromide. The suspension was stirred for 5 to 10 minutes and then treated with acetone and ether to obtain 0.6 g of dried cells.

A microbial electrode was assembled with the dried cell preparation. Concentration of L-glutamic acid in the L-glutamic acid fermentation broth samples as described in EXAMPLE 3 were measured. The resulted analytical values were in good agreement with those obtained according to the conventional autoanalyzer method in which the enzyme from pumpkin was used. In this case, no enzyme activity was detected in the cells without the surfactant treatment, with which the assay of L-glutamic acid was impossible.

EXAMPLE 6

E. coli ATCC 23226 was cultivated in a flask with shaking at 30° C. in a medium shown in Tab. 8. After 20-hour-cultivation, 50 ml of the cultured broth was centrifuged to harvest cells, which were washed well with 50 ml of 0.1 M KCl and lyophilized to give 0.6 g of lyophilized cells.

TABLE 8

| Composition of medium (pH 6.5) | |
|---|---|
| Component | Content (g/dl) |
| Glucose | 1.0 |
| Polypeptone | 1.0 |
| KH$_2$PO$_4$ | 0.5 |
| Yeast extract | 0.2 |
| L-Lysine HCl | 0.2 |
| Antifoam (Toshiba silicone) | 0.1 ml/l |

The lyophilized cells (1-2 mg) was suspended into a small amount of water to be paste (1), which was spread over a nylon mesh (1') (diameter: 10 mm). The mesh was fixed on a silicone membrane (3) of a dissolved carbon dioxide-sensitive electrode (Model E 5036, Radiometer Co., Denmark) with a cellophane membrane (2) as shown in FIG. 11.

The microbial electrode (10) was inserted into a flow cell (volume: 0.5 ml) through a rubber packing (12, 12') and a measuring system was assembled as shown in FIG. 12.

As a carrier fluid, 0.1 M pyridine-hydrochloric acid buffer solution, pH 5.00 (containing 0.5 g/dl NaCl, 0.5 g/dl KH$_2$PO$_4$ and 0.1 g/l pyridoxal-5'-phosphate) was fed from (15) at a flow rate of 4 ml/min and N$_2$ gas was also blown from (13') into the flow cell (11) at a flow rate of 0.2 l/min in FIG. 12. The electrode (10) was connected with a pH meter (18') and with a recorder (18) in order to measure the electromotive force. During the measurement, the temperature in the flow cell was maintained at 30° C. Aqueous 5 g/l L-lysine solution and its diluted sample was successively injected from the sample input (14) at a rate of 1 ml/min for 3 minutes.

The sample was diluted with the buffer solution and flowed into the flow cell (11). At the same time the microbial electrode (10) began to respond. The response reached a saturated level after 3 minutes and similar peaks to those as shown in FIG. 13 were recorded, in which the axis of ordinate and abscissa represent the electromotive force (mV) of the electrode and time, respectively. There was a relationship similar to one as shown in FIG. 4 between the height of the peak in FIG. 13 and the concentration of L-lysine in the flow cell (11). The linear response curve obtained had a slope of 58 mV/pC$_{Lys}$ which was almost in agreement with the coefficient of Nernst term in Equation (II) (theoretical value: 60.16 mV, (30° C.). *Brevibacterium lactofermentum* ATCC 13869 was cultivated at 30° C. with aeration and agitation in a medium shown in Tab. 9. During the cultivation 40 g/dl urea solution was added maintaining the pH of the broth at 6.5–8.0.

TABLE 9

| Composition of medium (pH 7.0) | |
|---|---|
| Component | Content |
| Glucose | 10.0 g/dl |
| KH$_2$PO$_4$ | 0.1 g/dl |
| Mg SO$_4$ 7H$_2$O | 0.1 g/dl |
| Thiamine HCl | 10 mg/dl |
| Soy bean hydrolysate (Mieki ®) | 1 ml/dl |

The cultured broth was diluted 20 times, which was Sample A. Various amounts of L-lysine of reagent grade were added to said Sample A, which were Sample B, C and D.

The peak heights were read with these samples according to the system shown in FIG. 12 and their L-lysine concentrations were determined using the calibration curve that was drawn by measuring the peak height of the standard solution according to the same system.

The results are given in Tab. 10. Each value of the sample was in good agreement with what was obtained by the conventional Warburg's manometer method in which the enzyme from *Bacterium cadaberis* was used.

TABLE 10

| Assay of L-lysine in cultured broth | | |
|---|---|---|
| | L-lysine concentration (g/dl) | |
| Sample | Method by the present invention | Warburg's manometer method (conventional method) |
| A | 1.32 | 1.32 |
| B | 3.44 | 3.40 |
| C | 5.86 | 5.89 |
| D | 6.50 | 6.45 |

EXAMPLE 7

*Lactobacillus casei* ATCC 7469 (Test No. 1) was cultivated with shaking in a medium containing 10% skim milk, 0.5% L-lysine hydrochloride and 100 mcg/l pyridoxal. *Strepto coccus faecalis* ATCC 12984 (Test No. 2), *Pseudomanas saccharophia* ATCC 15946 (Test No. 3), *Bacillus subtilis* ATCC 15037 (Test No. 4) and *Myxococcus virescens* ATCC 25203 (Test No. 5) were cultivated with shaking in a medium containing 1% meat extract, 1% polypeptone, 0.5% L-lysine hydrochloride and 100 mcg/l pyridoxal. *Aspergillus niger* ATCC 6278 (Test No. 6) was also cultivated with shaking in a Koji extract supplemented with 2% glucose, 0.1% KH$_2$PO$_4$ and calcium carbonate. After 24 hours-incubation, 50 ml of each cultured broth was centrifuged to harvest cells. The wet cells were washed twice with 0.1 M KCl and suspended into 5 ml of water. To the suspension was added 5 ml of acetone dropwise at room temperature and 0.5–0.6 g each of acetone-ether-treated cells was obtained according to the method as described in EXAMPLE 4 (About 10$^6$ cells/g of living cells was detected in the treated cell preparation by cultivating on a nutrient agar). Microbial electrodes were assembled with these active cell preparations in the same manner as described in EXAMPLE 4 and the L-lysine concentrations of the following L-lysine fermentation broth samples were determined. The resulted values coincided well with those obtained according to the conventional acidic ninhydrin method as shown in Tab. 11.

TABLE 11

| | Assay of L-lysine in L-lysine fermentation broths | | | | | | |
|---|---|---|---|---|---|---|---|
| | L-Lysine concentration (g/dl) | | | | | | |
| | Method by the present invention | | | | | | |
| Sample | Test No. | | | | | | Conventional acidic ninhydrin method |
| | 1 | 2 | 3 | 4 | 5 | 6 | |
| A | 2.54 | 2.49 | 2.53 | 2.55 | 2.49 | 2.50 | 2.54 |
| B | 3.60 | 3.59 | 3.64 | 3.63 | 3.64 | 3.65 | 3.62 |
| C | 4.20 | 4.21 | 4.24 | 4.24 | 4.25 | 4.21 | 4.25 |

EXAMPLE 8

*Streptococcus faecalis* ATCC 12984 was cultivated at 37° C. for 15 hours in a medium containing 3% casein hydrolyzed by trypsin, 1% glucose and 0.1% yeast autolysate. The harvested cells were treated in the same manner as described in EXAMPLE 4 to give 0.5 g of an acetone-ether-treated cell preparation, with which a microbial electrode was constructed. Various amounts of L-phenylalanine were added to L-glutamic acid fermentation broths, which were Sample A, B and C, respectively. The concentration of L-phenylalanine in each sample assayed with the electrode was compared with the value obtained by the liquid chromatography method. The value of each sample obtained by both methods was in good agreement respectively as shown in Tab. 12. The acetone-ether-treated cell preparation retained their activity for 6 months, although the activity of cell preparation without the treatment was kept only for 1 month in a refrigerator.

TABLE 12

Assay of L-phenylalanine in L-glutamic acid fermentation broth

| | L-Phenylalanine concentration (g/dl) | |
| --- | --- | --- |
| Sample | Method by the present invention | Liquid chromatography method |
| A | 0.82 | 0.83 |
| B | 1.88 | 1.92 |
| C | 2.95 | 3.00 |

EXAMPLE 9

*E. coli*. ATCC 10787 was cultivated in the same manner as described in EXAMPLE 8. The harvested cells were treated by the same way described in EXAMPLE 4 to obtain 0.3 of an acetone-ether-treated cell preparation. A microbial electrode was constructed with the treated cell preparation. Various amounts of L-arginine was added to L-glutamic acid fermentation broths, which were Samples A, B and C, respectively. The concentration of L-arginine in each sample was assayed by the method with the electrode according to the present invention, which was compared with the value obtained by the liquid chromatography method. The value obtained by broth methods was in good agreement respectively as shown in Tab. 13.

TABLE 13

Assay of L-arginine in L-glutamic acid fermentation broth

| | L-Arginine concentration (g/dl) | |
| --- | --- | --- |
| Sample | Method by the present invention | Liquid chromatography method |
| A | 1.25 | 1.15 |
| B | 6.37 | 6.44 |
| C | 10.56 | 10.85 |

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A microbial electrode for determining the concentration of an L-amino acid in a culture medium or a cultured broth solution, which comprises:

a carbon dioxide gas sensitive electrode having a carbon dioxide permeable membrane;

anaerobic containing means containing said membrane and capable of containing a portion of said broth or mixture;

a microorganism capable of anaerobically decarboxylating said L-amino acid immobilized on said membrane; and inert gas supplying means injectably attached to said containing means.

2. The electrode of claim 1 wherein said microorganism is a microbial cell.

3. The electrode of claim 2 wherein said microbial cell is selected from the group consisting of intact cells, freeze-dried cells, solvent treated cells, surface active agent treated cells, and mixtures thereof.

4. The electrode of claim 2 wherein said microbial cell is fixed in a carrier.

5. The electrode of claim 1 wherein said membrane is selected from the group consisting of dialysis membranes, semi-permeable membranes, Millipore filters and nylon nets having micropores capable of entrapping said microorganisms.

6. The electrode of claim 1 wherein said microorganism is selected from the group consisting of Escherichia coli ATCC 8739, Citrobacter freundii ATCC 10787, Clostridium welchii ATCC 13124, Rhodotorula glutinis IFO 0413, Escherichia coli ATTC 23226, Bacterium cadaveris ATCC 9760, Streptococcus faecalis ATCC 12984, Pseudononus saccharophia ATCC 16946, Bacillus subtilis ATCC 15037, and Lactobacillus casei ATCC 7469.

7. A system for determining the concentration of an L-amino acid in a culture medium or cultured broth, which comprises:

(a) a carbon dioxide gas sensitive electrode having a carbon dioxide permeable membrane;

(b) anaerobic containing means containing said membrane;

(c) a microorganism capable of anaerobically decarboxylating said L-amino acid immobilized on said membrane;

(d) anaerobic conveying means for anaerobically conveying a mixture of a sample of said L-amino acid and a buffered carrier solution saturated with an inactive gas to said containing means;

(e) sample supplying means for supplying a sample of said L-amino acid to said conveying means;

(f) buffered carrier solution supplying means for supplying a buffered carrier solution to said conveying means;

(g) inactive gas supplying means for supplying inactive gas to said conveying means; and (h) measuring means or recording means electrically connected to said carbon dioxide electrode.

* * * * *